United States Patent
Tseng et al.

(10) Patent No.: US 8,971,657 B2
(45) Date of Patent: Mar. 3, 2015

(54) METHOD FOR IMPROVING IMAGE QUALITY AND IMAGING SYSTEM USING THE SAME

(71) Applicant: Institute of Nuclear Energy Research Atomic Energy Council, Executive Yuan, Taoyuan County (TW)

(72) Inventors: Fan-Pin Tseng, Taipei (TW); Meei-Ling Jan, Taoyuan County (TW); Yu-Ching Ni, Taoyuan County, TX (US)

(73) Assignee: Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 36 days.

(21) Appl. No.: 13/962,029

(22) Filed: Aug. 8, 2013

(65) Prior Publication Data
US 2014/0133723 A1  May 15, 2014

(30) Foreign Application Priority Data
Nov. 9, 2012  (TW) .............................. 101141803 A

(51) Int. Cl.
G06K 9/00 (2006.01)
G06K 9/40 (2006.01)
G06T 5/00 (2006.01)
A61B 6/03 (2006.01)
A61B 6/00 (2006.01)

(52) U.S. Cl.
CPC ................ *G06T 5/003* (2013.01); *A61B 6/037* (2013.01); *A61B 6/5211* (2013.01); *A61B 6/5229* (2013.01); *A61B 6/5258* (2013.01); *G06T 2207/10081* (2013.01); *G06T 2207/10104* (2013.01); *G06T 2207/10108* (2013.01); *A61B 6/4417* (2013.01)
USPC .......................................... 382/254; 382/128

(58) Field of Classification Search
USPC .................................. 382/128–134, 254–275
See application file for complete search history.

(56) References Cited

U.S. PATENT DOCUMENTS

| 5,351,305 | A * | 9/1994 | Wood et al. ................... 382/128 |
| 5,737,456 | A * | 4/1998 | Carrington et al. ........... 382/299 |
| 5,790,709 | A * | 8/1998 | Kopeika et al. ............... 382/254 |
| 6,246,783 | B1 * | 6/2001 | Avinash ....................... 382/128 |
| 7,889,254 | B2 | 2/2011 | Kochi et al. |
| 2001/0008418 | A1 * | 7/2001 | Yamanaka et al. ............ 348/222 |
| 2002/0164082 | A1 * | 11/2002 | Sumitomo et al. ........... 382/254 |

OTHER PUBLICATIONS

Knoess, et al., "Performance evaluation of the microPET R4 PET scanner for rodents", May 2003, vol. 30, No. 5, European Journal of Nuclear Medicine and Molecular Imaging.

* cited by examiner

*Primary Examiner* — Alex Liew
(74) *Attorney, Agent, or Firm* — WPAT, PC; Justin King

(57) ABSTRACT

The invention provides a method for improving image quality. Through applying variation value during operation of iterated algorithm, this invention can reduce blur phenomenon caused by partial volume effects and improve image accuracy. In an embodiment, by applying the algorithm utilized in the method for improving image quality, this invention further provides an imaging system to detect the distribution of the object, thereby obtaining a clear restored image corresponding to the radiation source.

14 Claims, 10 Drawing Sheets

METHOD FOR IMPROVING IMAGE QUALITY AND IMAGING SYSTEM USING THE SAME

FIELD OF THE INVENTION

The present invention relates to a medical image processing technology, and more particularly, to a method for image quality improvement and an imaging system thereof.

BACKGROUND OF THE INVENTION

With rapid advance of technology, nuclear medicine imaging is becoming an effective diagnosis tool as it can be used for tracing a small amount of a radioisotope when the radioisotope is being dosed into a patient and permits specific physiological processes to be scrutinized at region of interest. The common devices that are used for nuclear medicine imaging are positron emission tomography (PET) instruments and single photon emission computed tomography (SPECT) instruments, just to name a few.

Taking SPECT for example, SPECT imaging is performed by using an imaging scanner to acquire multiple 2-D images from multiple angles. Thereafter, a computer is used to apply a image reconstruction algorithm to the multiple images, yielding a 3-D dataset. This dataset may then be manipulated to show thin slices along any chosen axis of the body. Nevertheless, during the image reconstruction, image degradation is generally induced due to the limited spatial resolution of the instrument used for acquiring the images, and thus the image quantitative accuracy can be adversely affected.

Assuming the image being detected is represented by the function g(x, y), the image degradation model can be represented by the following function:

$$g(x,y)=H[f(x,y)]+n(x,y);$$

wherein, f(x, y) represent an original image,
H represents a degradation function; and
n(x, y) represents noise.

For simplicity, H is generally assumed to be a linear spatial invariant, and thereby, the foregoing image degradation model is represented as following:

$$g(x,y)=h(x,y)*f(x,y)+n(x,y),$$

wherein, the symbol "*" represents a mathematical operation of convolution; and the convolution in spatial domain and the multiplication in frequency domain make up a Fourier pair.

The Fourier transformation for the aforesaid image degradation model in frequency domain is represented as following:

$$G(u,v)=(u,v)*F(u,v)+N(u,v).$$

Thereafter, the foregoing function of frequency domain is transformed back into a function of spatial domain that can be calculated using less time and resource. In a nuclear medical imaging application, when the original image f(x, y) is a point object, the application of h(x, y) upon the point object is going to cause an extended blur blob in an image that the original image is degenerated and spread. Consequently, the degradation function h(x, y) is called a point-spread function. The purpose of an image restoration operation is to acquire a measurement to an original image, so that it is preferred to have more information to the degradation function h(x, y) and the noise function n(x, y).

Generally, for improving the resolution of quantitative analysis, a technique of image restoration is adopted for image quality enhancement, whereas such image restoration technique is being referred as de-blurring. The algorithms used for enabling image restoration can be divided into two categories according to their difference in nature, which are the direct method and the iteration method. Among which, the direct methods attempt to solve the problem by a finite sequence of operations so as to deliver an exact solution of the original image for the image degradation model, while the iterative method is a mathematical procedure that generates a sequence of improving approximate solutions to the original image. The most common iteration algorithm used is the Lucy Richardson (LR) algorithm.

For instance, an LR method for restoring degraded nuclear medical image is described in U.S. Pat. No. 7,899,254. The Richardson Lucy algorithms an iterative procedure for restoring a latent image that has been blurred by a known point spread function that is based upon the maximum likelihood estimation, and consequently, the following equation is used:

$$f^{(k+1)}(x, y) = f^{(k)}(x, y)\left[h(-x, -y) * \frac{g(x, y)}{g^{(k)}(x, y)}\right]$$

wherein $g^{(k)}(x,y)=h(x,y)*f^{(k)}(x,y)$

The concept of the aforesaid algorithm originated by treating an image data as a random quantity that is a statistical possibility resulting from other random quantities, whereas the aforesaid algorithm is performed to achieve a maximum value of that statistical possibility. It is noted that to enabling the aforesaid algorithm, all the pixel values of image data must be positive.

The biggest problem to the conventional LR algorithm is that: the LR algorithm assume that the degradation function h(x, y) is a linear spatially invariant, however, although the degradation in a nuclear medical image appears to be distributed according to a Gaussian distribution, the degradation function h(x, y) should be a spatial variable. Please refer to FIG. 1, which is curve diagram showing a measurement resolution of degradation for a microPET R4 system according to the paper, entitled "Performance evaluation of the microPET R4 PET scanner for rodents", by Knoess C., Eur J Nucl Med Mol Imaging, 30(5), pp. 737-47, 2003. As shown in FIG. 1, the farther from the center of the system the blur become, and it will be a very time-consuming task if one intends to restore the blurred image pixel by pixel using their respective corresponding degradation functions. Taking a 512×512 image for example, there will be 262144 degradation functions that the time required for restoring the image can be multiplied. For saving time, conventionally the 512×512 image is divided into several sub-images and only some of the sub-images that contain vital information are selected for restoration. Another problem for the conventional LR algorithm is that: for different positions or objects in an image, the optimum number of iteration may not be the same. For instance, the objects that are comparatively smaller in an image may suffer more serious partial volume effect and thus may require more iterations in the LR algorithm to restore. Therefore, it is difficult to restore all aspect in one image by a fixed iteration number.

Therefore, it is require a method for image quality improvement and an imaging system thereof for solving the aforesaid shortcomings of the conventional LR algorithm.

SUMMARY OF THE INVENTION

The primary object of the present invention is to provide a method for image quality improvement and an imaging system thereof, in which a function variable t is used, and by the interpolation or extrapolation with respect to the variable t, the relationship between various degradation functions for different positions in an image and an image restoring process can be achieved, thereby, the time for the image restoring process can be shortened and the conventional problem relating to spatial variable can be solved.

Another object of the present invention object of the present invention is to provide a method for image quality improvement and an imaging system thereof, in which the function variable t for image restoring is defined to be the multiplication of a volume variable tb that is related to volume of objects in an image with a degradation function ta describing the degradations for different positions in the image, and the function variable t used in an image restoration can work for either suppressing or accelerating the effect of iteration while improving the accuracy of image quantitative analysis.

In an exemplary embodiment, the present invention provides a method for image quality improvement, which comprises the steps of:
  providing an imaging device configured with a degradation function h(x, y) relating to each detection position (x, y) on a detection plane;
  using the degradation function h(x, y) to determine position variables (ta) as each of the position variables (ta) is corresponding to a degradation distance measured between each detection position (x, y) and a datum position on the detection plane;
  using the imaging device to image at least one emission source on the detection plane so as to generate a measured image g(x, y) composed of a plurality of pixels accordingly, while allowing the plural pixels to be arranged corresponding the detection positions (x, y) of the detection plane in respective and one of the plural pixels to be arranged corresponding to the datum position;
  performing an image restoration operation on each pixel of the measured image g(x, y) based upon the measured image g(x, y) and the degradation function h(x, y) so as to generate an initial restored image f(x, y); and
  for each pixel in the measured image g(x, y), performing an iterated algorithm at the detection position (x, y) corresponding thereto using the following formula:

$$f_{k+1}(x, y) = (1-t)f_k(x, y) + t\left[h(-x, -y) * \frac{g(x, y)}{h(x, y) * f_k(x, y)}\right]f_k(x, y),$$

wherein, t is a function variable that is the multiplication of a volume variable tb with a position variable ta, and thus, obtaining an iterated restored image $f_{k+1}(x, y)$ after k iterations.

In another exemplary embodiment, the present invention provides an imaging system, which comprises: an imaging device, configured with a degradation function h(x, y) relating to each detection position (x, y) on a detection plane, for imaging at least one emission source on the detection plane so as to generate a measured image g(x, y) composed of a plurality of pixels accordingly, while allowing the plural pixels to be arranged corresponding the detection positions (x, y) of the detection plane in respective and one of the plural pixels to be arranged corresponding to the datum position; a storage unit, for storing position variables (ta) as each of the position variables (ta) is corresponding to a degradation distance measured between each detection position (x, y) and a datum position on the detection plane; a control unit, for determining the degradation distances for each detection position (x, y) based upon the distances measured respectively between each of the plural pixels and the pixel that is arranged corresponding to the datum position so as to be used for determining the position variables (ta) for their corresponding pixels, and for performing an image restoration operation on each pixel of the measured image g(x, y) based upon the measured image g(x, y) and the degradation function h(x, y) so as to generate an initial restored image f(x, y), and for each pixel in the measured image g(x, y), enabling the control unit to perform an iterated algorithm at the detection position (x, y) corresponding thereto using the following formula:

$$f_{k+1}(x, y) = (1-t)f_k(x, y) + t\left[h(-x, -y) * \frac{g(x, y)}{h(x, y) * f_k(x, y)}\right]f_k(x, y)$$

wherein, t is a function variable that the multiplication of a volume variable tb with a position variable ta, and thus, obtaining an iterated restored image $f_{k+1}(x, y)$ after k iterations.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 2:
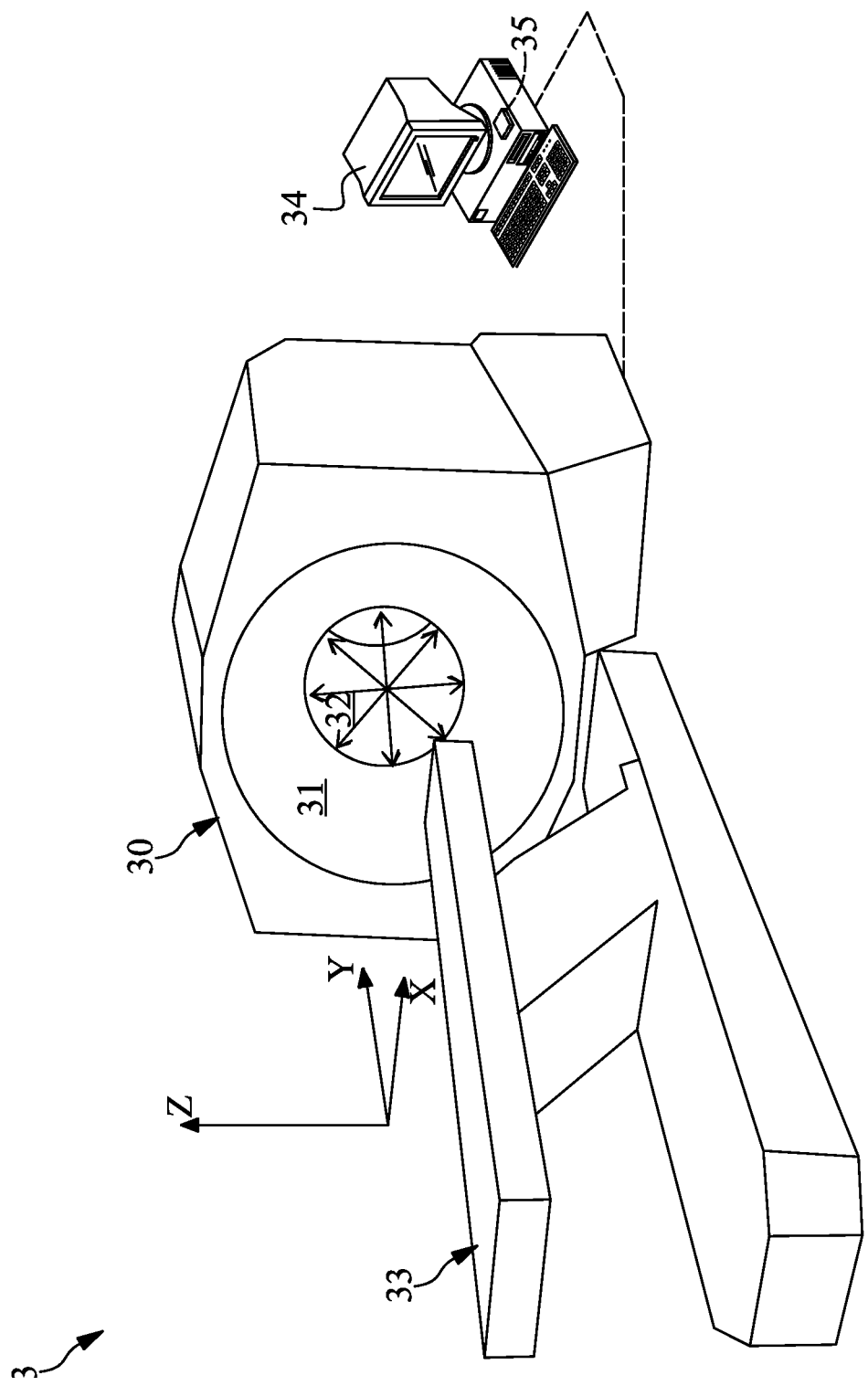
FIG. 2 is a schematic view of a tomography imaging system.

Please refer to FIG. 2, which is a schematic view of a tomography imaging system. It is noted that the imaging system used in the present invention can be an X-ray imaging system, a computed tomography (CT) system, a positron emission tomography (PET) system, a single photon emission computed tomography (SPECT) system or a tomosynesis system, but is not limited thereby. In this embodiment, a microPET R4 system by Concorde Micro System Co. is used for illustration. As shown in FIG. 2, the tomography system 3 has an imaging device 30, which is configured with a circular detection module 31 for allowing an object to be detected or a patient on a movable carrier 33 to enter the hollowed area 32 of the circular detection module. In addition, the detection module 31 has a plural pairs of detectors that are used for detecting positron pairs or single-photons, that are known to those skilled in the art and thus will not be described further herein. It is noted that the detection module 30 is not necessary to be formed into the circular structure, and thus it can be composed of a plurality of detectors that are arranged in pairs at opposite positions and moved in a linear movement relative to each other. Moreover, the imaging device 30 is configured with a degradation function h(x, y) relating to each detection position (x, y) on a detection plane, and is used for imaging at least one emission source on the detection plane so as to generate a measured image g(x, y) composed of a plurality of pixels accordingly, while allowing the plural pixels to be arranged corresponding the detection positions (x, y) of the detection plane in respective and one of the plural pixels to be arranged corresponding to the datum position.

The imaging device 30 further comprises: a control unit 34 and a storage unit 35. The control unit 34 can be a device with calculation ability, such as a computer or a server, and can be an internal unit integrated inside the imaging device 30 or an external device. The control unit 34 is electrically connected to the storage unit 35 and the detection module 31. The storage unit 353, being a hard disk or a memory module, is used for storing a position variable (ta) as the position variables (ta) is corresponding to a degradation distance measured between each detection position (x, y) and a datum position on the detection plane.

Figure 1:
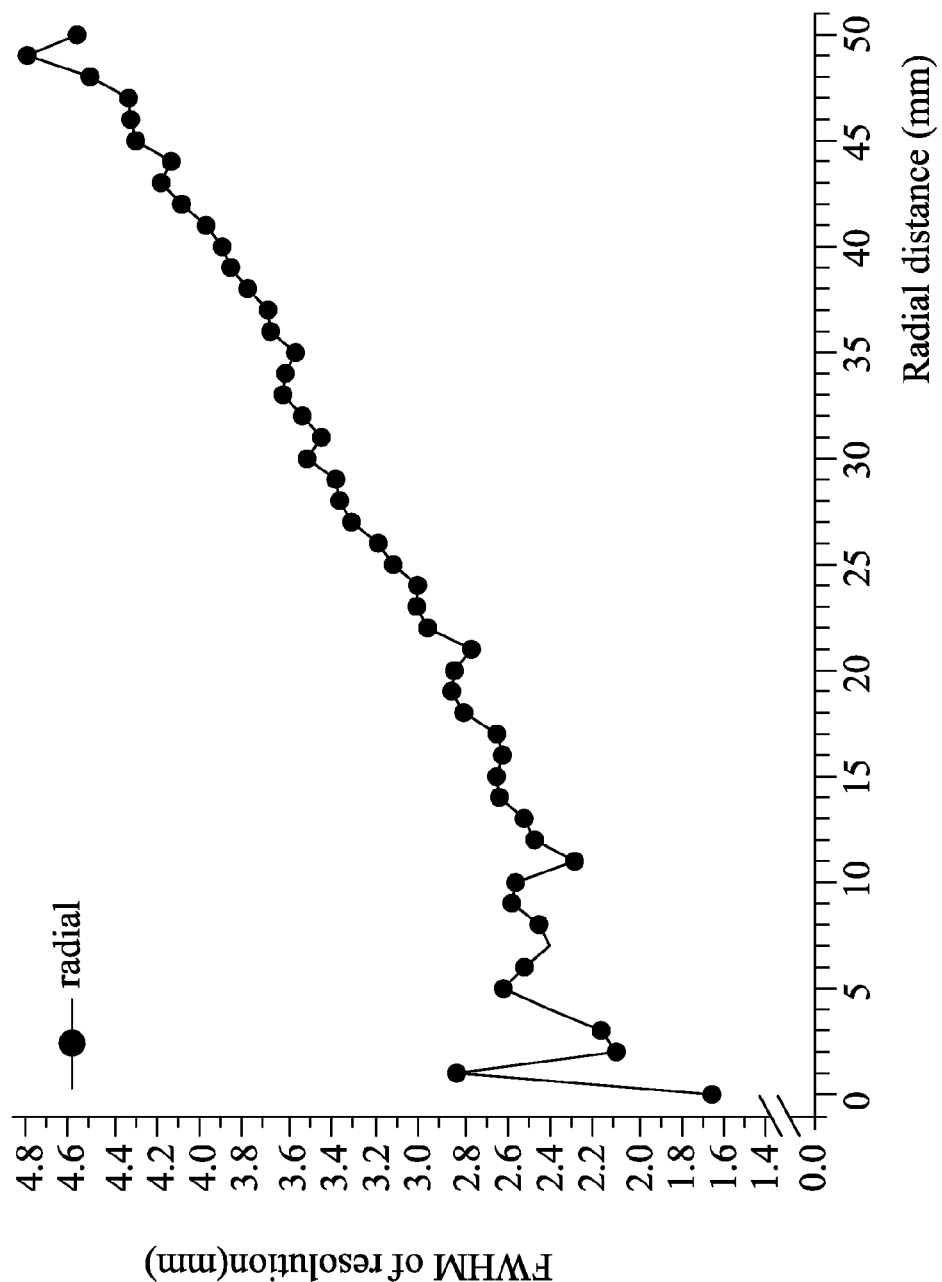
FIG. 1 is curve diagram showing a measurement result of degradation for a conventional imaging system.

The degradation function the tomography system can be represented using the curve diagram of FIG. 1. Generally, for any type of tomography system, there will be a specific degradation function provided therefore by its manufacturer. The degradation function is defined to be a curve describing the relationship between a value of full width half maximum (FWHM) relating to the resolution of the imaging device and a distance measured between each detection position (x, y) and the center of the detection plane. In this embodiment, the datum position is the center of the detection plane of the tomography system. For the system shown in FIG. 2, the detection plane is a XZ plane of a XYZ Cartesian coordinate system that is a circular slice defined inside the hollow of the circular detection module. It is noted that there can be more than one detection plane that are distributed one after another along the Y axis, and the amount of the detection plane is determined according to the size of the detector array in the detection module. In addition, the degradation distance is a radial distance measured between each detection position (x, y) and the datum position on the detection plane.

Figure 3:
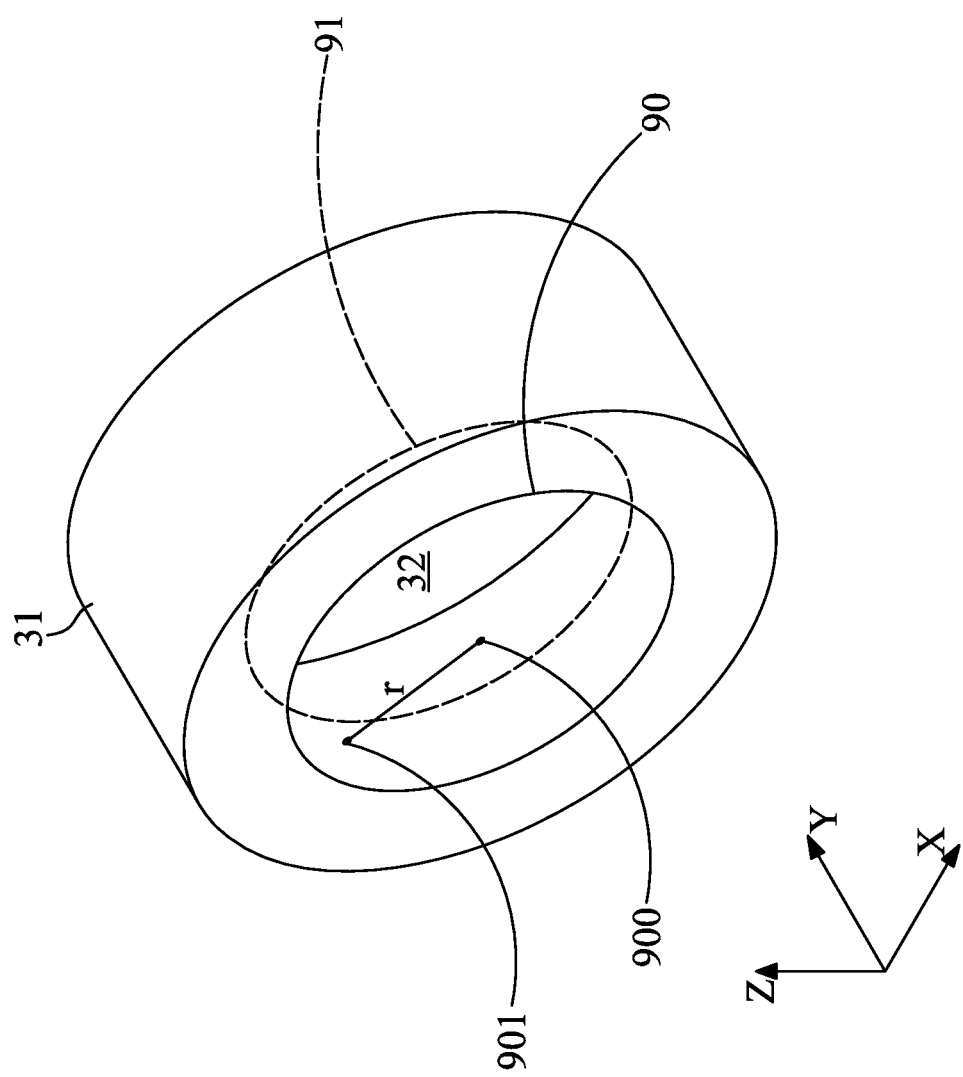
FIG. 3 is a schematic diagram showing a measurement of a degradation distance.

Please refer to FIG. 3, which is a schematic diagram showing a measurement of a degradation distance. As the detection module 31 shown in FIG. 3, there can be a plurality of detection planes defined and distributed one after another along the Y axis inside the hollowed area 32 of the detection module 31, and in this embodiment, there are two such detection planes 90 and 91 used for illustration. For the detection plane 90, the degradation distance is the radial distance r measured between the position 901 and the datum position 900, i.e. the center of the detection plane 90. Although the datum position is defined to be the center of the detection plane, it is not limited thereby and can be defined at any position by users as required. Furthermore, since the plural pixels in a restored image is arranged corresponding the detection positions (x, y) of the detection plane in respective and one of the plural pixels to be arranged corresponding to the datum position, therefore the degradation distance for each pixel can be determined according to the aforesaid relationship between the detection positions and the datum position.

Before describing the way for obtaining the position variable (ta), the principle of the Lucy Richardson (LR) algorithm is provided as following:

$$f^{(k+1)}(x, y) = f^{(k)}(x, y)\left[h(-x, -y) * \frac{g(x, y)}{g^{(k)}(x, y)}\right] \quad (1)$$

wherein, $g^{(k)}(x,y) = h(x,y) * f^{(k)}(x,y)$, $f^{(k+1)}(x, y)$ represents the grey value of each pixel in the restored image after k iterations.

In the conventional LR algorithm, the degradation function h(x, y) is assumed to be a linear spatially invariant. However, as indicated in FIG. 1, the degradation phenomenon in nuclear imaging is generally appeared to be a Gaussian distribution, that is a problem of spatially variant. As each pixel $f^{(k+1)}(x, y)$ is corresponding to one detection position on a detection plane of a tomography system, whereas the radial distance between each detection position and the datum position is corresponding to value of full width half maximum (FWHM), as shown in FIG. 1, each pixel $f^{(k-1)}(x, y)$ in a restoration process is corresponding to one specific degradation function.

For simplicity, each pixel $f^{(k+1)}(x, y)$ in the restored image adopts the degradation function of the datum position as the degradation function corresponding thereto. However, for introducing the concept of the degradation function being a spatial variable into the restoration algorithm, a function variable (t) is introduced for spatial variable adjustment. Accordingly, an deduction can be provided as following:

$$\begin{aligned}f_{k+1}(x, y) &= (1-t)f_k(x, y) + t\left[h(-x, -y) * \frac{g(x, y)}{h(x, y) * f_k(x, y)}\right]f_k(x, y) \\ &= f_k(x, y)\left[(1-t) + t\left[h(-x, -y) * \frac{g(x, y)}{h(x, y) * f_k(x, y)}\right]\right] \\ &= f_k(x, y)\left[t\left[h(-x, -y) * \frac{g(x, y)}{h(x, y) * f_k(x, y)} - 1\right] + 1\right] \\ &= f_k(x, y)\left[1 + t\left[h(-x, -y) * \frac{g(x, y)}{h(x, y) * f_k(x, y)} - 1\right]\right] \\ &= f_k(x, y) - tf_k(x, y)\left[1 + h(-x, -y) * \frac{g(x, y)}{h(x, y) * f_k(x, y)}\right]\end{aligned}$$

From the foregoing deduction, an image restoration algorithm capable of overcoming the conventional linear spatially invariant problem is provided as following:

$$f_{k+1}(x, y) = (1-t)f_k(x, y) + t\left[h(-x, -y) * \frac{g(x, y)}{h(x, y) * f_k(x, y)}\right]f_k(x, y) \quad (2)$$

According to the aforesaid deduction, the image restoration algorithm of the present invention introduces a function variable (t) into the conventional LR algorithm after each iteration for compensation so as to obtain a restored image $f^{(k+1)}(x, y)$. In an embodiment of the present invention, the function variable (t) is the multiplication of a volume variable (tb) with a position variable (ta), in which the volume variable (tb) can equal to 1 when the effect of the volume of the emission source to the restored image is not to be taken into consideration. The position variable (ta) can be obtained from the curve of FIG. 1 in a manner that a value of FWHM is obtained according to a distance measured between each detection position (x, y) and the datum position of the detection plane, and then the obtain FWHM value is divided by 2.35 so as to obtain a blur sigma σ, thereby, a corresponding position variable (ta) can be obtained from the curve of FIG. 4 based upon the blur sigma σ.

Figure 4:
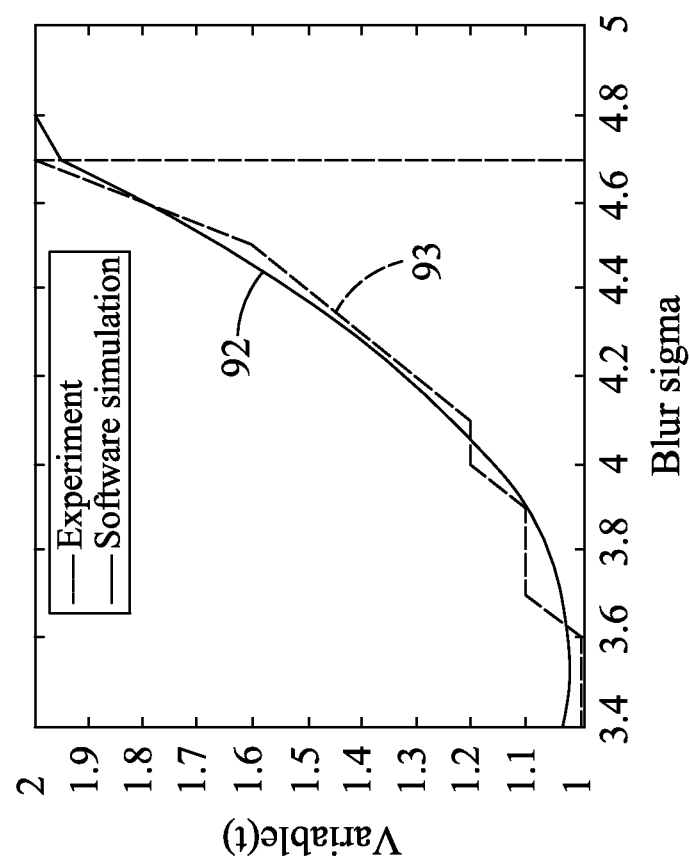
FIG. 4 is a curve diagram showing the relationship between value of blur sigma (σ) and position variables (ta).
Figure 5A:
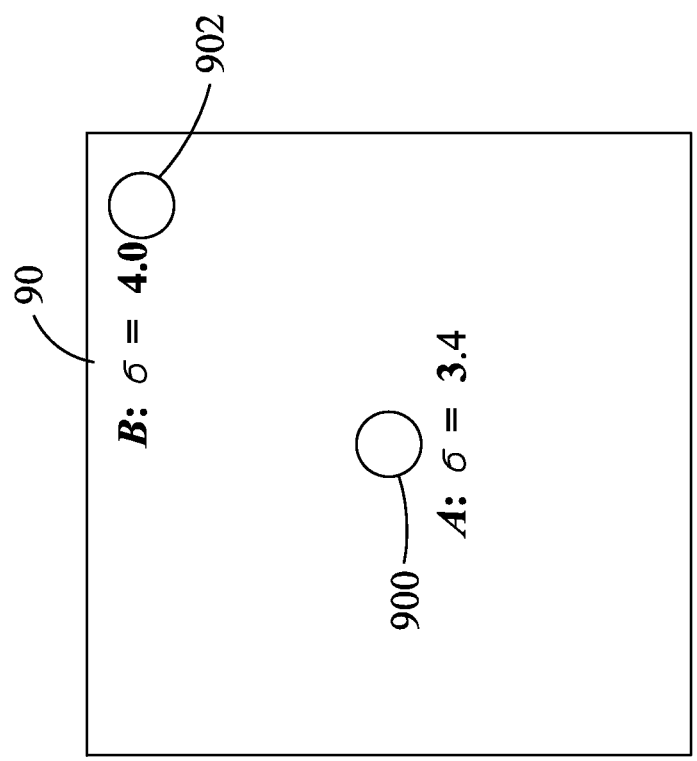
FIG. 5A and FIG. 5B are schematic diagrams showing steps for determining position variables (ta).
Figure 5B:
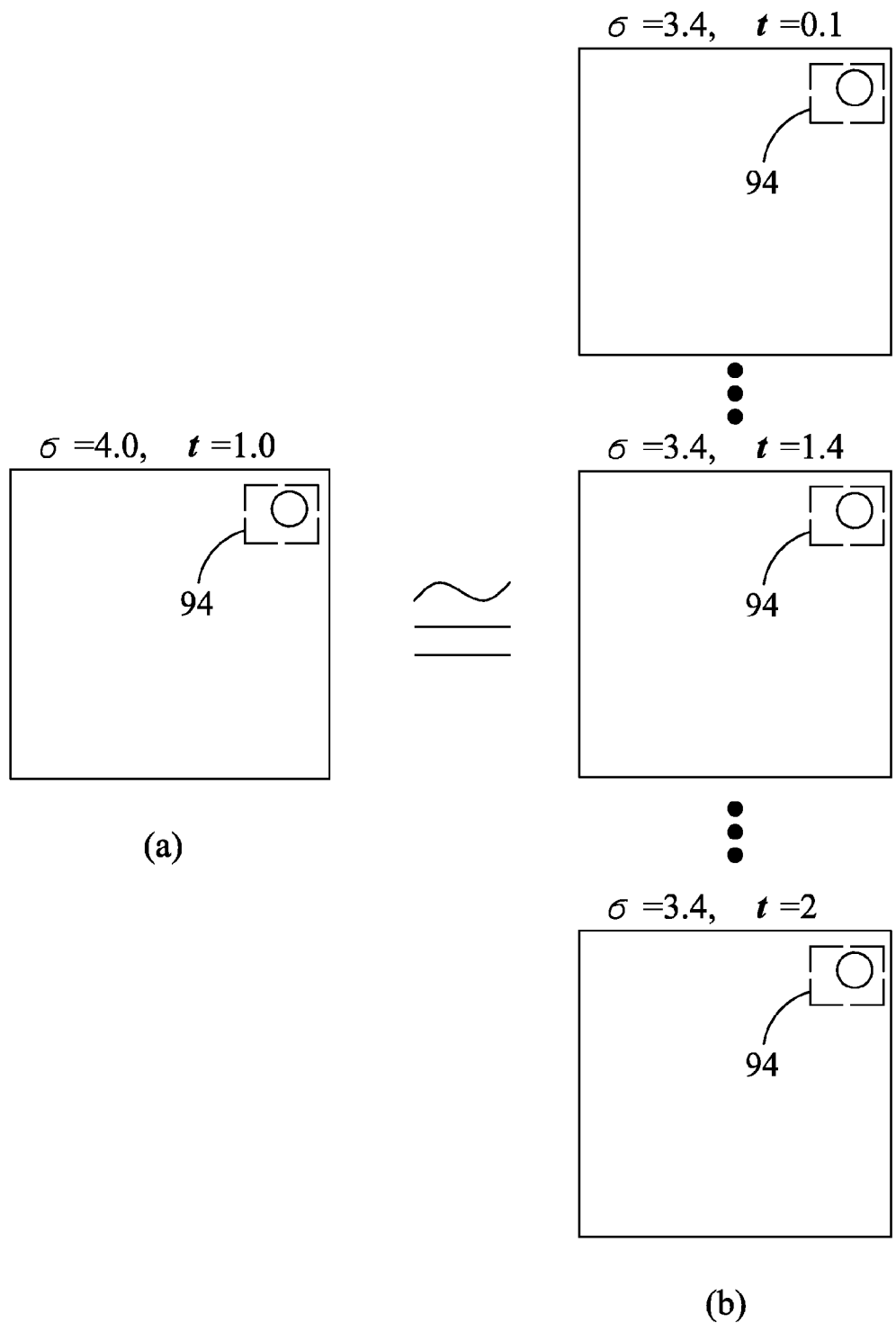

The curves of FIG. 4 can be generated experimentally or by a computer simulation. In FIG. 4, the curve 92 is obtained from a software simulation while the curve 93 is obtained experimentally. The curve 93 is obtained using a software, which is programmed to perform monte carlo simulations to a point source so as to obtain different degradations of the point source at different detection positions in a tomography system. In this embodiment, a microPET R4 system is used for illustration. It is generally known to those skilled in the art to program and use a software to simulation the degradation of a specific tomography system, and thus the programming and operation of the software will not be further described herein, In the computer simulation, the software can automatically place the point source at any possible location in the tomography system while simultaneously simulating the detection of a microPET R4 system for obtaining a counting with respect to the point source, and consequently obtaining the degradation curve of FIG. 1. After the degradation curve relating to the relationship between detection position and FWHM values through the computer simulation, σ values for every detection position on the detection plane can be obtained. Thus, up to this point, the obtained a values represent the inputs required in the calculation of the LR algorithm for the degradation function h(x, y) corresponding to each pixel in the restored image. For defining the relationship between the function variable (t) and the blur sigma σ, please refer to the diagrams shown in FIG. 5A and FIG. 5B. since the various σ values with respect to different detection positions in a tomography system can be obtained through monte carlo simulations, in the embodiment shown in FIG. 5A that the σ value for the point A on a detection plane is 3.4, whereas the point A is located at the center of the detection plane, and the σ value for the point B on a detection plane is 4.0. Generally speaking, the σ value at the center is usually smaller, while those near the edge are larger.

Thereafter, for the emission source located at the position 902, its σ value is defined to be 3.4, and then an image restoration is performed using the formula (2) with the input of different t. For instance, in a condition when the degradation of the point A which is the center of the detection plane is used as a standard and its σ value is measured to be 3.4 while the σ value for the point B is 4.0, in order to define the value of variable t for the position 902 for image restoration, an object with a radius that is larger than 2 times the system FWHM value is placed at the position 902 for simulating a degradation phenomenon (σ=4). Then, an image restoration is performed using the formula (2) with σ=4 and t=1, while defining a region of interest (ROI) 94 so as to obtain the diagram (a) of FIG. 5B. Thereafter, enabling the value of t to vary from 0 to 2, while defining σ=3.4 in the ROI 94, the diagrams (b) of FIG. 5B can be obtained. Eventually, by selecting one image form those diagrams (b) whose restoration result is most approximate to the diagram (a), the value t of that selected diagram (b) is selected. Taking the aforesaid diagrams for example, the restoration using σ=3.4 and t=1.4 is most approximate to those of σ=4 and t=1, thereby the relationship between the degradation function and the variable t at position 902 can be defined. Similarly, the same result can be obtained experimentally using almost the same procedures. However since it is difficult to perform the experiment for every detection position on the detection plane, thus a curve fitting method is adopted for compensating experimental error from discrete sampling so as to achieve a relationship between t and σ as shown in FIG. 4.

It is noted that the function variable (t) equals the multiplication of a volume variable (tb) with a position variable (ta), and in one aforesaid embodiment, the volume variable (tb) is defined to be 1. However, the volume variable (tb) is not necessary to be 1, and the following description provides a way addressing the condition when the volume variable (tb) is not equal to 1. When the factor of volume variable (tb) is taken into account in the function variable (t), it is in a condition when the volume of an emission source is smaller than 2 times the FWHM relating to the resolution of the imaging device, since in such condition it is difficult to obtain a clear image after LR image restoration until the amount of iteration is increased. However, the increasing in iteration number might cause other emission sources of different volumes to deform in the image restoration process. Thus, for addressing such problems, especially when there are a plurality of emission sources of different volumes, the idea of volume variable (tb) is used for compensation so as to achieve clear images for all emission sources.

Figure 6:
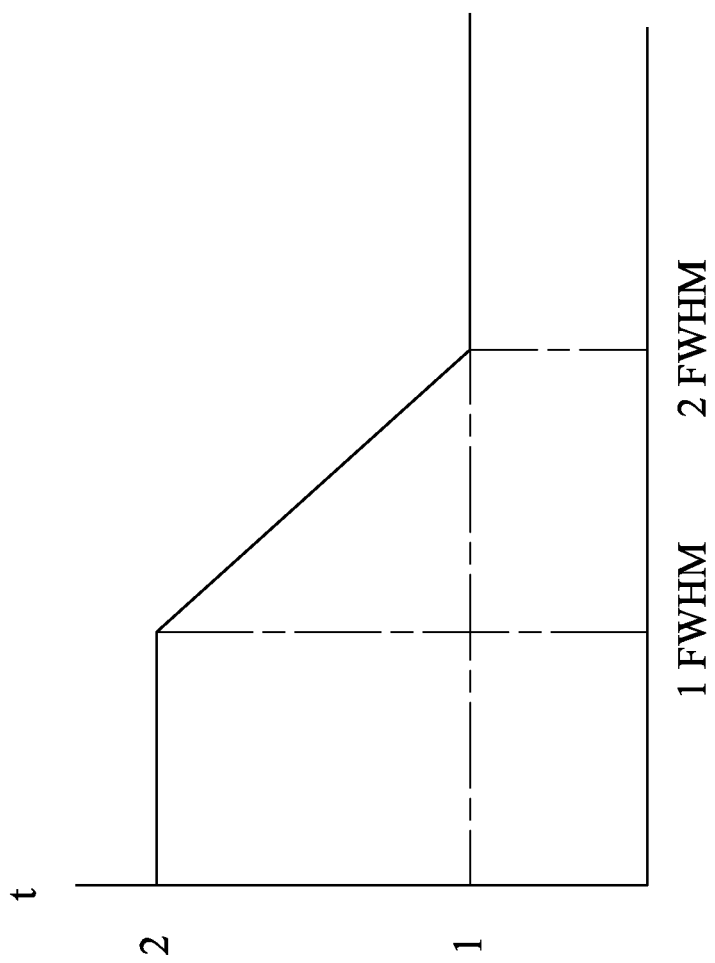
FIG. 6 is a diagram for determining volume variables (tb).

In order to determine the volume variable (tb), the degradation function h(x, y) should be obtained first, whereas the degradation function h(x, y) is defined to be a curve describing the relationship between a value of full width half maximum (FWHM) relating to the resolution of the imaging device and a distance measured between each detection position (x, y) and the center of the detection plane. Similarly, the degradation function can be obtained either through monte carlo simulations or through experiments, as shown in FIG. 1. Then, the volume variable (tb) is enabled to varied and reduced from 2 to 1 according to a specific variation relationship, and while the FWHM relating to the resolution of the imaging device is ranged within a specific amplification range, the volume variable (tb) is defined to be 1 when the FWHM relating to the resolution of the imaging device exceeds the specific amplification range, as shown in FIG. 6. It is noted that the amplification range of the FWHM is not limited to be between 1 and 2, and can be defined at will according to actual requirement. In addition, in another embodiment of the invention, the image width of each emission source is determined according to the relating image acquired by an imaging device, whereas the imaging device can be a computed tomography (CT) device, or a magnetic resonance imaging (MRI) device. Therefore, if there are volume information that can be obtained in CT imaging or MRI imaging, such volume information can be transformed into system FHWM.

Figure 7:
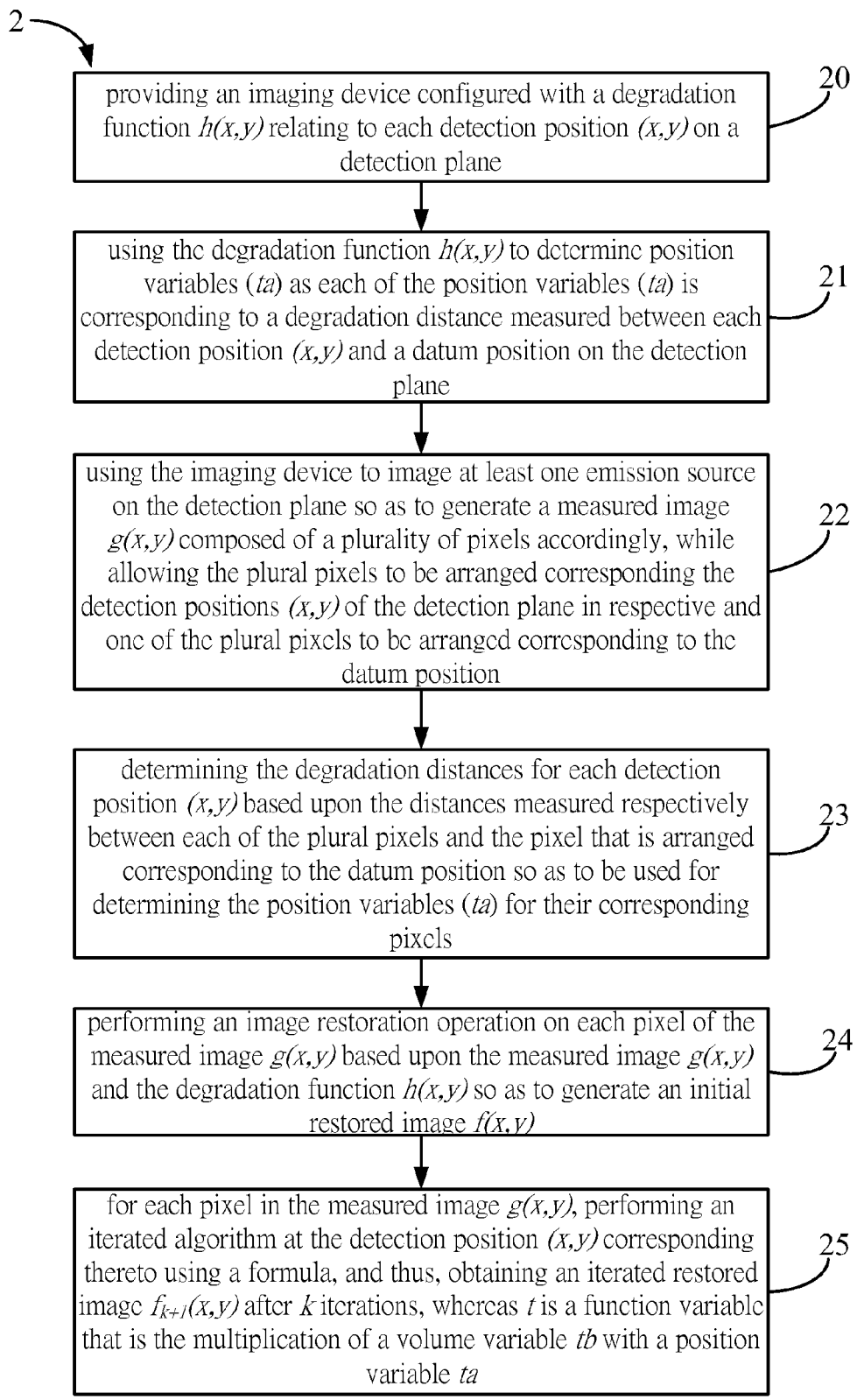
FIG. 7 is a flow chart depicting steps performed in a method for image quality improvement.

Please refer to FIG. 7, which is a flow chart depicting steps performed in a method for image quality improvement. As shown in FIG. 7, the method for image quality improvement 2 starts from the step 20. At step 20, an imaging device is provided, which is configured with a degradation function h(x, y) relating to each detection position (x, y) on a detection plane, whereas the imaging device is a micorPET R4 system 30 shown in FIG. 2 and the degradation function h(x, y) is the curve shown in FIG. 1; and then the flow proceeds to step 21. At step 21, the degradation function h(x, y) is used to determine position variables (ta) as each of the position variables (ta) is corresponding to a degradation distance measured between each detection position (x, y) and a datum position on the detection plane; and then the flow proceeds to step 22. In addition, in the step 21, the degradation distance is a radial distance measured between each detection position (x, y) and the datum position on the detection plane, as indicated in FIG. 3. Taking the system shown in FIG. 2 for example, all the data obtained at step 21 is stored in the storage unit 35, while the storage unit 35 can be an internal device integrated inside the control unit 34 or an external device.

At step 22, the imaging device is used to image at least one emission source on the detection plane so as to generate a measured image g(x, y) composed of a plurality of pixels accordingly, while allowing the plural pixels to be arranged corresponding the detection positions (x, y) of the detection plane in respective and one of the plural pixels to be arranged corresponding to the datum position; and then the flow proceeds to step 32. In addition, in the step 22, the object to be detected or the patient is transported to be moved inside the hollowed area of the imaging device 30 for allowing the detection module 31 to project positrons or single-photons thereto and then receiving a counting signal accordingly which is then to be transmitted to the control unit 34 for processing so as to obtain the measured image g(x, y).

At step 23, the degradation distances for each detection position (x, y) are determined based upon the distances measured respectively between each of the plural pixels and the pixel that is arranged corresponding to the datum position so as to be used for determining the position variables (ta) for their corresponding pixels; and then the flow proceeds to step 24. In this step, as each detection position is corresponding to one image pixel, and thereby, the control unit 34 is able to calculate the distance between each pixel and the datum position, so as to be used in an calculation according the data obtained from the step 21 for determining the position variable (ta).

At step 24, an image restoration operation is performed on each pixel of the measured image g(x, y) based upon the measured image g(x, y) and the degradation function h(x, y) so as to generate an initial restored image f(x, y); and then the flow proceeds to step 25. In this step, the initial restored image f(x, y) is obtained using an LR image restoration algorithm. At step 25, for each pixel in the measured image g(x, y), an iterated algorithm is performed at the detection position (x, y) corresponding thereto using a formula (2), and thus, obtaining an iterated restored image $f_{k+1}(x, y)$ after k iterations, whereas t is a function variable that is the multiplication of a volume variable (tb) with a position variable (ta). It is noted that the restored image $f_{k+1}(x, y)$ is the restored image being improved by the formula (2).

It is noted that the iteration number k can be determined according to actual requirement and the condition of the restored image quality, and the product of the iteration number k and the function variable (t) is a constant value. For instance, the image quality of a restored image of 6 iterations and t=1 is about the same as that of 4 iterations and t=1.5. Nevertheless, in a condition when overly image restoration happened even only after 1 or 2 iterations which is often in SPECT, one can address the issue by decreasing the value of the function variable t so as to prevent the overly image restoration from happening at such early stage of iteration. Thus, by adjusting the iteration number k and the function variable (t), an overly image restoration phenomenon caused by the iterated algorithm is prevented. Thus, by adjusting the iteration number k and the function variable (t), an overly image restoration phenomenon caused by the iterated algorithm is prevented.

In addition, it is noted that the foregoing embodiments mainly describe the condition when the volume variable (tb) is defined to be 1, that is, the effect of the emission source' volume upon the image restoration is not taken into account. However, in another embodiment of the present invention, the effect of the emission source' volume is considered and thus the value of the volume variable (tb) is determined by the diagram illustrated in FIG. 6. After the volume variable (tb) is determined, the function variable (t) can be obtained by multiplying the volume variable (tb) with the position variable (ta). Thereby, even the emission sources that are comparatively small in size can be seen clearly in the restored image. Especially when there are a plurality of emission sources of different volumes, the idea of volume variable (tb) is used for compensation so as to achieve clear images for all emission sources.

Figure 8A:
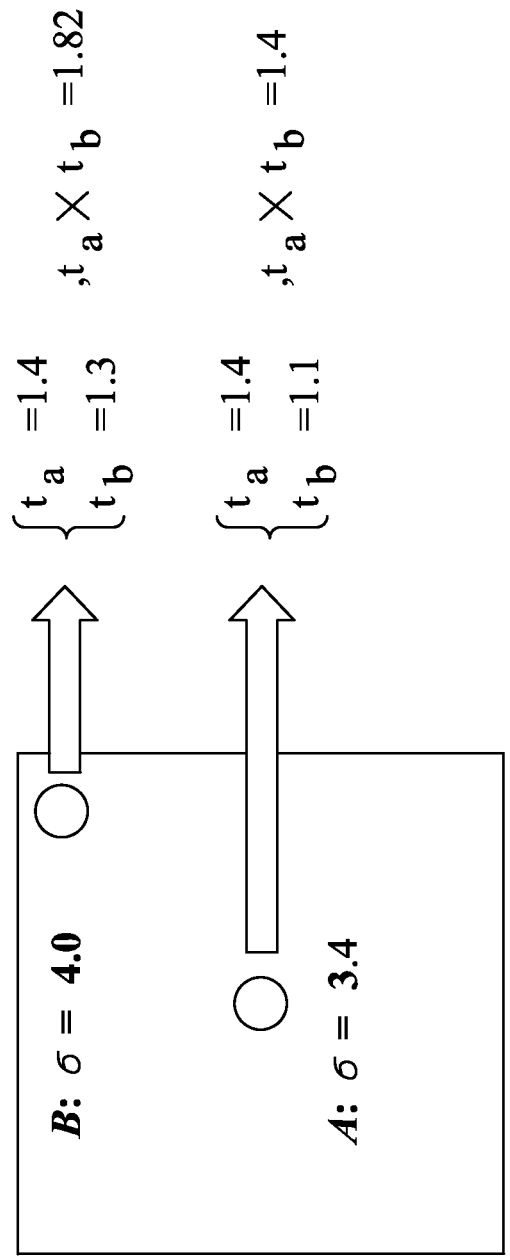
FIG. 8A and FIG. 8B are schematic diagrams showing the relationship between iteration number and the corresponding function variable (t).
Figure 8B:
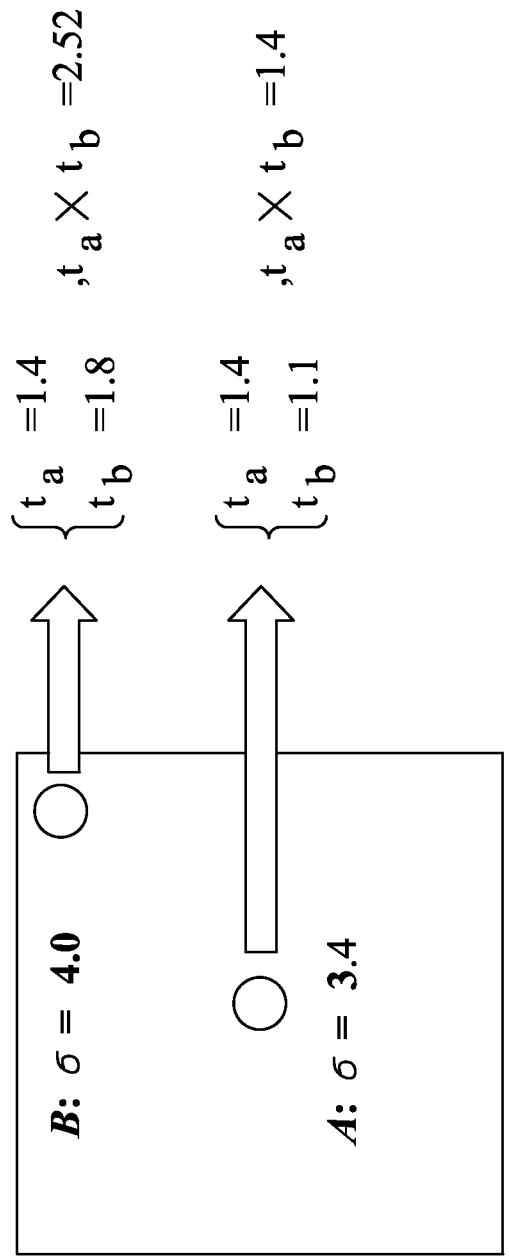

However, since the product of the two variables can be a number larger than 2, that is the function variable (t) is larger than 2, it is required to apply the principle of "the product of the iteration number k and the function variable (t) is a constant value" for increasing the iteration number k so as to enable the function variable (t) to decrease, enabling the iteration of the LR algorithm to converge. As shown in FIG. 8A, at both detection position A and B, their corresponding value of ta×tb are smaller than 2 and thus those variables can be used directly in the image restoration process without adjustment. One the other hand, for the two detection positions A and B shown in FIG. 8B, the product of ta and tb for the detection position B is larger than 2, and thus it is required to adjust the iteration number k so as to decrease the function variable (t). In FIG. 8B, ta×tb=2.52 at the detection B, and assuming the iteration number k is set to be 5, the constant value K from the principle of "the product of the iteration number k and the function variable (t) is a constant value" can be obtained as following: 2.52 (t)×5 (k)=12.6 (K), so that the constant value K is 12.6. Accordingly, for decreasing the function variable (t) to a value smaller than 2, the value of iteration (k) should be increased while maintaining the constant value K unchanged. In an embodiment, the value of t is divided by 2, i.e. t is decreased to 1.26, and consequently the iteration number k is increased to 10, as indicated in the following formula:

$$\left(\frac{2.52}{2}\right)(t) \times (5 \times 2)(k) = 12.6(K).$$

It is noted that the function variable (t) can be divided by any divisor only if the divisor is larger enough for decreasing the function variable (t) to a value smaller than 2. In addition, except for the detection position B in FIG. 8B, all the function variables (t) for other detection positions in FIG. 8B should be divided by the same devisor used for the detection position B simultaneously, that is, in this embodiment, they all required to be divided by 2 while enabling the corresponding iteration number to be increased by 2 times.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A method for image quality improvement, comprising the steps of:
    providing an imaging device configured with a degradation function h(x, y) relating to each detection position (x, y) on a detection plane;
    using the degradation function h(x, y) to determine position variables (ta) as each of the position variables (ta) is corresponding to a degradation distance measured between each detection position (x, y) and a datum position on the detection plane;
    using the imaging device to image at least one emission source on the detection plane so as to generate a measured image g(x, y) composed of a plurality of pixels accordingly, while allowing the plural pixels to be arranged corresponding the detection positions (x, y) of the detection plane in respective and one of the plural pixels to be arranged corresponding to the datum position;
    determining the degradation distances for each detection position (x, y) based upon the distances measured respectively between each of the plural pixels and the pixel so as to be used for determining the position variables (ta) for their corresponding pixels;
    performing an image restoration operation on each pixel of the measured image g(x, y) based upon the measured image g(x, y) and the degradation function h(x, y) so as to generate an initial restored image f(x, y); and
    for each pixel in the measured image g(x, y), performing an iterated algorithm at the detection position (x, y) corresponding thereto using the following formula:

$$f_{k+1}(x, y) = (1-t)f_k(x, y) + t\left[h(-x, -y) * \frac{g(x, y)}{h(x, y) * f_k(x, y)}\right]f_k(x, y),$$

wherein, t is a function variable that is the multiplication of a volume variable tb with a position variable ta, and thus, obtaining an iterated restored image $f_{k+1}(x, y)$ after k iterations.

2. The method of claim 1, wherein the variation of the function variable (t) is ranged between 0 and 2.

3. The method of claim 1, wherein the degradation function h(x, y) used in the restoration operation and the iterated algorithm is the degradation function h(x, y) corresponding to the datum position.

4. The method of claim 1, wherein the product of the iteration number k and the function variable (t) is a constant value.

5. The method of claim 4, wherein by adjusting the iteration number k and the function variable (t), an overly image restoration phenomenon caused by the iterated algorithm is prevented.

6. The method of claim 1, wherein the value of the volume variable (tb) is 1.

7. The method of claim 1, wherein the value of the volume variable (tb) is determined according to the following steps:
    acquiring the degradation function as the degradation function is defined to be a curve describing the relationship between a value of full width half maximum (FWHM) relating to the resolution of the imaging device and a distance measured between each detection position (x, y) and the center of the detection plane;
    enabling the volume variable (tb) to varied and reduced from 2 to 1 according to a specific variation relationship while the FWHM relating to the resolution of the imaging device is ranged within a specific amplification range, and enabling the volume variable (tb) to be 1 when the FWHM relating to the resolution of the imaging device exceeds the specific amplification range;
    making an evaluation to determine whether the width of each source in an image falls within the specific amplification range of the FWHM; and
    making an evaluation to determine whether each image width of each emission source falls within the specific amplification range of the FWHM relating to the resolution of the imaging device; and
    determining the volume variable (tb) according to the specific variation relationship and a value within the specific amplification range selected corresponding to the image widths when the width of each emission source in an image falls within the specific amplification range of the FWHM.

8. The method of claim 7, wherein the specific amplification range is defined to be a range between a value of 1 times the FWHM relating to the resolution of the imaging device and a value of 2 times the FWHM relating to the resolution of the imaging device.

9. The method of claim 7, wherein the width of each emission source in an image is determined based upon the image of the referring emission source in the measured image g(x, y).

10. The method of claim 7, wherein the width of each emission source in an image is determined based upon an image of the referring emission source that is acquired using an imaging device.

11. The method of claim 10, wherein the imaging device is a device selected from the group consisting of: a computed tomography (CT) device, and a magnetic resonance imaging (MRI) device.

12. The method of claim 1, wherein in a condition when the value of the function variable (t) is larger than 2, then the iteration number k is adjusted according to a principle of: "the product of the iteration number k and the function variable (t) is a constant value", so as to enable the value of the function variable (t) to decrease to a value smaller than 2.

13. An imaging system, comprising:
    an imaging device, configured with a degradation function h(x, y) relating to each detection position (x, y) on a detection plane, for imaging at least one emission source on the detection plane so as to generate a measured image g(x, y) composed of a plurality of pixels accordingly, while allowing the plural pixels to be arranged corresponding the detection positions (x, y) of the detection plane in respective and one of the plural pixels to be arranged corresponding to the datum position;
    a storage unit, for storing a position variable (ta) as the position variables (ta) is corresponding to a degradation distance measured between each detection position (x, y) and a datum position on the detection plane;
    a control unit, for determining the degradation distances for each detection position (x, y) based upon the distances measured respectively between each of the plural pixels and the pixel that is arranged corresponding to the datum position so as to be used for determining the position variables (ta) for their corresponding pixels, and for performing an image restoration operation on each pixel of the measured image g(x, y) based upon the measured image g(x, y) and the degradation function h(x, y) so as to generate an initial restored image f(x, y), and for each pixel in the measured image g(x, y), enabling the control unit to perform an iterated algorithm at the detection position (x, y) corresponding thereto using the following formula:

$$f_{k+1}(x, y) = (1-t)f_k(x, y) + t\left[h(-x, -y) * \frac{g(x, y)}{h(x, y) * f_k(x, y)}\right]f_k(x, y)$$

wherein, t is a function variable that the multiplication of a volume variable tb with a position variable ta, and thus, obtaining an iterated restored image $f_{k+1}(x, y)$ after k iterations.

14. The imaging system of claim 13, being a system selected from the group consisting of: an X-ray imaging system, a computed tomography (CT) system, a positron emission tomography (PET) system and a single photon emission computed tomography (SPECT) system.

* * * * *